United States Patent [19]

Baroncelli et al.

[11] Patent Number: 4,463,099
[45] Date of Patent: Jul. 31, 1984

[54] IMMUNOFLUORESCENCE REAGENTS, AND THE METHOD FOR THEIR PREPARATION

[75] Inventors: Vittorio Baroncelli; Claudio Colapicchioni; Ivo Giannini; Filippo Porcelli, all of Rome, Italy

[73] Assignee: Anic S.p.A., Palermo, Italy

[21] Appl. No.: 419,053

[22] Filed: Sep. 16, 1982

[30] Foreign Application Priority Data

Sep. 25, 1981 [IT] Italy ................ 24161 A/81

[51] Int. Cl.³ .............. G01N 33/58; G01N 33/54; G01N 33/52
[52] U.S. Cl. .................. 436/546; 260/112 R; 260/112 B; 436/800
[58] Field of Search ............ 436/546, 800; 260/112 B, 112 R

[56] References Cited

U.S. PATENT DOCUMENTS

| | | | |
|---|---|---|---|
| 2,937,186 | 5/1960 | Burckhalter et al. | 436/546 |
| 3,028,397 | 4/1962 | Tsou | 436/546 |
| 4,225,485 | 9/1980 | Buckler et al. | 436/800 |
| 4,238,395 | 12/1980 | Buckler et al. | 436/800 |
| 4,297,273 | 10/1981 | Buckler et al. | 436/800 |
| 4,351,760 | 9/1982 | Khanna et al. | 436/546 |

FOREIGN PATENT DOCUMENTS 2912845 10/1980 Fed. Rep. of Germany ...... 436/546

Primary Examiner—Christine M. Nucker
Attorney, Agent, or Firm—Hedman, Gibson, Costigan & Hoare

[57] ABSTRACT

New immunofluorescence reagents prepared by reacting together a protein, a cross-linking agent and a dye, which are of general formula

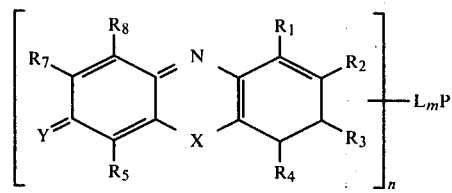

and which fluoresce between 600 and 900 nm.

11 Claims, 2 Drawing Figures

IMMUNOFLUORESCENCE REAGENTS, AND THE METHOD FOR THEIR PREPARATION

In clinical diagnosis the quantitative determination of small compounds such as hormones, drugs or metabolytes by immunological methods is extremely important. One of the methods for quantifying immunoreactions is to mark the antigens and antibodies with fluorescent chromophores such as fluorescein or rhodamine isothiocyanate. The main problem connected with the use of this method is the inherent fluorescence of the biological samples. In this respect, many substances such as the flavins, pyridine coenzymes and serum proteins fluoresce intensely in those regions of the spectrum in which the fluorochromes normally used as probes also emit. The use of probes which fluoresce in the red-near infrared region (600-900 nm), and thus fairly distant from the inherent fluorescence of the samples under examination (300-450 nm), would enable the background due to natural substances to be eliminated, and the sensitivity of the method to be increased. Many dyes which are free in solution are known to have these spectral properties, even though their intensity of fluorescence is fairly weak, but what is not obvious is that they maintain these properties if their structure is altered in some way by a covalent bond with another molecule.

Figure 1:
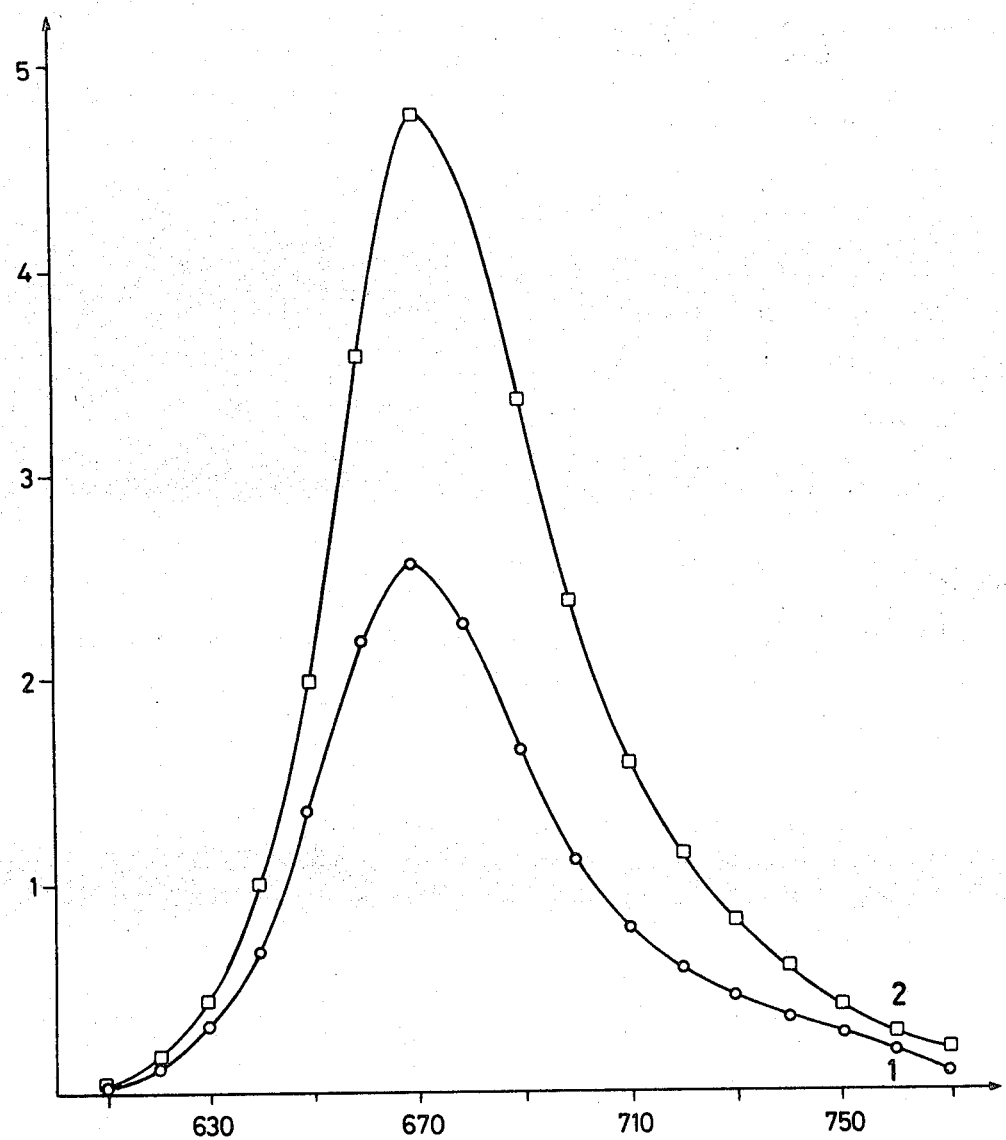
Figure 2:
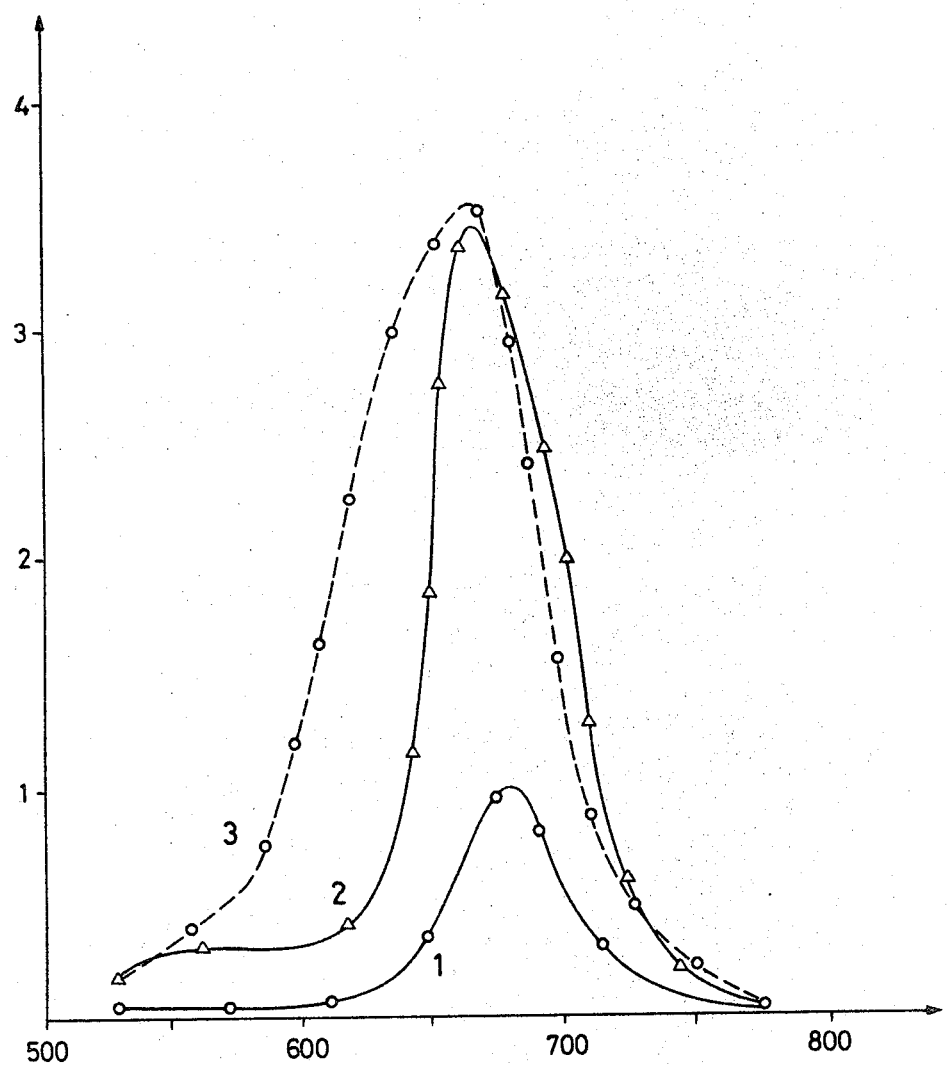

This result has now been obtained, and forms the subject matter of the invention, by covalently bonding dyes which fluoresce in the near-infrared region to various proteins by using bifunctional reagents which react with $-NH_2$ groups of the fluorochromes, without these dyes losing their spectural characteristics and in fact improving them by increasing fluorescence by 2 to 4 times (see FIG. 1 and FIG. 2).

FIG. 1 shows the emission spectra of an anti γ immunoglobulin-Nile blue conjugate (curve 2) and a Nile blue solution (curve 1).

The chromophore concentration is $2 \times 10^{-6}$M. The excitation wavelength is 600 nm.

The spectra were determined by a Perkin-Elmer MPF-2A spectrofluorometer fitted with a HAMAMATSU R446 photomultiplier. The abscissa axis represents the wavelength in nm, and the ordinate axis represents the fluorescence in arbitrary units. FIG. 2 shows the emission spectra of Protein A—Nile blue (curve 3) and HCS—Nile blue (curve 2) conjugates, and free Nile blue (curve 1), obtained by excitation at λ=515 nm with an Argon laser. The chromophore concentration is $6 \times 10^{-6}$M. The abscissa axis represents the wavelength in nm, and the ordinate axis the fluorescence in arbitrary units.

Generally, the bifunctional reagent, represented by the crosslinking agent, reacts directly both with the protein and with the dye to form complexes of general formula

[Dye]̄ₙLₘ Protein

If this is a carbodiimide, then because these reagents act by activating the carboxyl groups to give rise to a carbamido bond between the carboxyl groups and the amino group of the dye, complexes are obtained of general formula

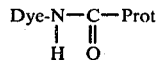

The protein part of these conjugates also maintains its biological characteristics, for example immunological if an antigen or antibody.

It should be noted that the use of these immunofluorescence reagents presents no particular difficulties in terms of instruments because it is necessary only to fit an infrared-sensitive photomultiplier to a normal spectrofluorometer. Measurements of particular sensitivity can be made by exciting the fluorochrome with a continuous or pulsed laser of red light or near-infrared, such as a helium-neon laser, a ruby laser or more easily a dye laser.

The use of these conjugates, in particular fluorescent antibodies, in microscopy presents no difficulty because only an infrared-sensitive film may be necessary. It also offers the advantage of being able to discriminate in the same microscopic preparation with respect to zones coloured with antibodies marked with conventional fluorochromes which fluoresce in the green-yellow region of the spectrum. The present invention therefore relates to new immunofluorescence reagents of general formula

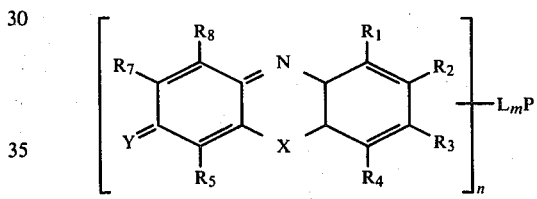

in which
n is a whole number from 1 to 4
m is a whole number equal to n, except when the cross-linking reagent is a carbodiimide, in which case m=0.
P is a protein
L is a cross-linking agent residue
X is an oxygen or sulphur atom
y is a group chosen from NH, $NH_2$, NR', NR'R" where R' and R", which may be the same or different, are alkyl, aryl, arylalkyl or alkylaryl radicals, possibly substituted, or an OCOR' group where R' has the aforesaid meaning
$R_1$, $R_2$, $R_3$, $R_4$, $R_5$, $R_7$, $R_8$, which may be the same or different, are either a hydrogen atom or an amino group or an alkyl, aryl, alkylaryl or arylalkyl radical, possibly substituted; $R_1$ and $R_2$ and/or $R_7$ and $R_8$ can also be bivalent radicals which close together to thus form a condensation ring with the cycloaromatic.

At least one of these (most frequently $R_3$) must be an amino group which on reacting with the cross-linking reagent gives rise to a —NH—L or —N=L—group.

These reagents are prepared by reacting together at least one compound chosen from each of the following classes
(a) a protein
(b) a dye chosen from those oxazines or thiazines having an absorption in the visible range with λ max between 550 and 800 nm, and having at least one free NH₂ and a fluorescence with emission between 600 and 900 nm (c) a cross-linking agent, generally bifunctional reagents of which the groups are able to react with the amino group of the dye.

Some compounds are listed hereinafter by way of example which can form part of the aforesaid classes.

Protein (i) Protein A from Staphylococcous aureus
(ii) Protein hormone
(iii) γ-immunoglobulin (Ig) of the various classes IgG, IgM, IgA, IgD, IgE.

Dye (i) Nile blue (C.I. 51180)

(ii) Cresyl violet (iii) Toluidine blue (C.I. 52040)

(iv) Brilliant cresyl blue (C.I. 51010)

Cross-linking agent (i) diisocyanate of general formula O=C=N—R—N=C=O where R is an alkyl, aryl, alkylaryl or arylalkyl radical, possibly substituted (ii) carbodiimide of general formula R—N=C=N—R' where R, R' are alkyl, aryl, alkylaryl or arylalkyl radicals, possibly substituted, and can be the same or different (iii) dialdehydes of general formula CHO—R—CHO where R is an alkyl, aryl, alkylaryl or arylalkyl radical, possibly substituted (iv) ethylene-maleic anhydride copolymers (EMA) of general formula (v) dinitrobenzenes of general formula The reaction between the three compounds can either be carried out starting from the substrates alone, or can be carried out in the presence of a medium compatible with the components, for example water, aqueous solutions of one or more salts, or buffer mixtures. The pH of the medium can vary from 4.5 to 9.5, and in addition small quantities of organic solvents can be added in order to increase the solubility of the dye. The reaction temperature varies around ambient temperature (from 4°–5° C. to the protein denaturation temperature).

The reaction is generally carried out with a large excess of dye over the protein, in order to prevent protein-protein reactions, this excess varying from 4 to 50 times in terms of molar concentration.

The reaction is also carried out with a large excess of crosslinking agent over the total quantity of protein plus dye.

All operating details will be apparent from the following examples.

These examples do not however limit the invention, which can be advantageously applied to any three substrates.

EXAMPLE 1

The immunoglobulin fraction of an anti human immunoglobulin G rabbit serum (anti h IgG) was marked both with Nile blue (CI 51180) and with toluidine blue (CI 52040), using glutaraldehyde as the bifunctional reagent.

Glutaraldehyde is added to a solution containing 2 mg of anti h IgG and $1.3 \times 10^{-4}$ mmoles of Nile blue or toluidine blue in 1 ml of potassium phosphate buffer (0.01M pH 7.1) until the final glutaraldehyde concentration is 0.05%.

The reaction is allowed to proceed for 30 minutes under stirring at ambient temperature, and is then blocked by trapping the free aldehyde groups with sodium bisulphite. The unreacted dye is eliminated by chromatography over Sephadex G25.

In a typical experiment, a fluorescent anti h IgG—Nile blue conjugate is obtained with a molar protein:dye ratio of 1:1.8, or an anti h IgG—toluidine blue conjugate with a molar ratio of 1:1.2.

The dye concentration was calculated using for the Nile blue a molar extinction coefficient of $5.8 \times 10^4$ at $\lambda = 635$ nm, and for the toluidine blue a molar extinction coefficient of $3.1 \times 10^4$ at $\lambda = 620$ nm.

The protein concentration was calculated using a $\epsilon\% = 14$ at $\lambda = 280$ nm, and correcting for dye absorption in the ultraviolet, or by determining the nitrogen with the Kjeldahl micromethod.

Both the conjugates significantly maintain the antibody property of bonding human immunoglobulins.

EXAMPLE 2

A conjugate between human chorionic somatomammotropin (HCS) and a dye of the oxazine series, namely brilliant cresyl blue (CI 51010), is prepared using glutaraldehyde as the reagent. Glutaraldehyde is added to 1 ml of sodium phosphate buffer at pH 7.8, 0.05 M containing 2.5 mg of HCS and $5 \times 10^{-4}$ mmoles of dye, until the final glutaraldehyde concentration is 0.1%. After 1 hour of reaction at ambient temperature, the solution is treated as in example 1 to obtain a conjugate with a molar HCS:brilliant cresyl blue ratio of 1:1.

The ratio was calculated using for the dye a molar extinction coefficient of 16500 at $\lambda = 633$, and for the HCS a $\epsilon\% = 8.3$ at $\lambda = 278$.

EXAMPLE 3

Using glutaraldehyde as the cross-linking agent, then under the same experimental conditions as example 1 a conjugate is prepared between Nile blue and Protein A from Staphylococcus aureus.

The molar protein-dye ratio of this conjugate is 1:1.5. In the case, when not using the Kjeldahl micromethod, a $\epsilon\% = 1.65$ at $\lambda = 275$ was used for determining the Protein A.

EXAMPLE 4

Nile blue (CI 51180) is used for marking anti human immunoglobulin (anti h IgG), using as the bifunctional reagent toluylene-2,4-diisocyanate (TDIC), of which the structural formula is

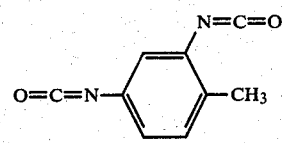

The reaction proceeds in two steps. In the first, the isocyanate group in position 4, which is less sterically committed, reacts with the NH$_2$ of the anti hIgG.

In the second step, Nile blue is added at 37° C. to the anti hIgG-TDIC conjugate containing no free TDIC, so that the second isocyanate group reacts with the amino group of the dye.

Step 1

0.05 ml of TDIC are added to a solution of 5 mg of γ-immunoglobulin in potassium phosphate buffer of pH 7.5, 0.05M, cooled to 0° C. The reaction is allowed to proceed for about 30 minutes at 0° C. under vigorous stirring, the mixture then being centrifuged to remove the unreacted diisocyanate which precipitates in aqueous solutions at 0° C. The supernatant is allowed to incubate again at 0° C. for a further hour, in order to enable any dissolved TDIC to react.

Step 2

0.1 ml of phosphate buffer containing $10^{-4}$ mmoles of Nile blue are added to the solution of step 1. The resultant solution is kept at 37° C. for 1 hour under stirring, and is then dialysed against 0.1M ammonium carbonate in order to destroy any unreacted isocyanate group. The free dye is removed by dialysis against distilled water or neutral buffer followed by chromatography over Sephadex G25.

The resultant conjugate has a molar portein:Nile blue ratio of 1:2.4, calculated using the methods and extinction coefficients for protein and dye given in example 1.

The fluorescence intensity of this conjugate (see FIG. 1) is much higher than that obtained on exciting the free chromophore at the same concentration.

EXAMPLE 5

Nile blue (CI. 51180) is conjugated with Protein A from Staphylococcus aureus using 1-ethyl-3-(3-dimethylaminopropyl)carbodiimide (ECDI), of which the structural formula is

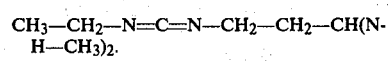

50 mg of ECDI are added to a solution containing 5 mg of Protein A and an excess of Nile blue to the extent of about ten times molar in 1.2 ml of distilled water. The reaction is allowd to proceed under stirring for seven hours at ambient temperature, while maintaining the pH between 6 and 6.8 by adding dilute HCl, after which the product is dialysed against 4–5 water changes over 48 hours. The colloidal suspension which can form in the dialysis bag is eliminated by centrifuging, and any free dye still in solution is removed by chromatography over Sephadex G25.

The Nile blue concentration in the conjugate is determined using a molar extinction coefficient in water of $5.8 \times 10^4$ at $\lambda = 635$. The protein concentration is calculated using a $\epsilon\% = 1.65$ at $\lambda = 275$ nm and correcting for the dye absorption in the ultraviolet or, in a more precise manner, by determining the nitrogen with the Kjeldahl micromethod. In a typical reaction, a conjugate is obtained with a molar Protein A: Nile blue ratio of 1:1 ÷ 1.5 (this ratio can be varied by varying the reaction time and temperature) and a fluorescence intensity at $\lambda = 680$ nm which is greater than that obtained by exciting the free chromophore at the same concentration. The Protein A marked in this manner maintains its property of bonding immunoglobulins, as demonstrated by the passive hemoagglutination test, comprising agglutination of ram erythrocytes sensitised with rabbit G immunoglobulins by Protein A—Nile blue.

EXAMPLE 6

A protein hormone, namely human chorionic somatomammotropin (HCS) is marked with Nile blue in the presence of ECDI using the procedure illustrated in example 5, to which reference should be made for details.

The reagent concentrations are 2.5 mg of HCS, $10^{-3}$ mmoles of Nile blue dissolved in 0.05 ml of ethanol, and 45 mg of ECDI, all in 2 ml of water.

The protein concentration is determined using a $\epsilon\% = 8.3$ at $\lambda = 278$.

The fluorescent conjugate obtained has a molar HCS:dye ratio of 1:1, and the hormone maintains its antigen properties when incubated with an anti HCS antiserum.

EXAMPLE 7

Toluidine blue (CI 52040) is used to mark rabbit γ-immunoglobulins using ECDI.

The reaction conditions are as follows.

The reaction mixture, consisting of 3 mg of γ-immunoglobulins and $2 \times 10^{-4}$ mmoles of toluidine blue in 2 ml of water is adjusted to pH 5.6 by dilute HCl. 25 mg of ECDI are added, and the reaction is allowed to proceed under stirring at ambient temperature. After about 2 hours, a further 25 mg of ECDI are added, and the reaction is allowed to proceed for a further 2 hours.

The solution is finally dialysed against water or a neutral buffer of low ionic force for 48–72 hours with various changes. Using a molar extinction coefficient of $3.1 \times 10^4$ for the dye at $\lambda = 620$ nm, and a $\epsilon\% = 14$ for the protein at $\lambda = 280$ nm, a molar protein: toluidine blue ratio of 1:1.1 is calculated for the prepared conjugate.

The $\gamma$-immunoglobulin marked in this manner maintains its immunological properties in the presence of anti $\gamma$-immunoglobulin.

I claim:

1. Immunofluorescence reagents of general formula

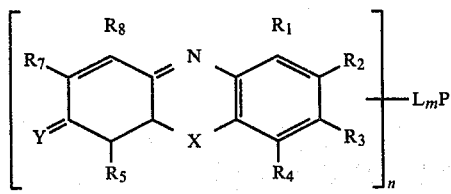

in which
n is a whole number between 1 and 4
n is a whole number equal to n or o
P is a protein
L is the residue of a cross-linking agent
X is an oxygen or sulphur atom
Y is a group chosen from NH, $NH_2$, NR' and NR'R'', where R' and R'', which can be the same or different, are substituted and unsubstituted alkyl, aryl, arylalkyl or alkylaryl radicals, or a OCOR' group where R' has the aforesaid meaning;
$R_1$, $R_2$, $R_3$, $R_4$, $R_5$, $R_7$ and $R_8$, which can be the same or different, are either a hydrogen atom or an amino group or a substituted or unsubstituted alkyl, aryl, alkylaryl or arylalkyl radical, or $R_1$ and $R_2$ and/or $R_7$ and $R_8$ are bivalent radicals which close together to thus form a condensation ring with the cycloaromatic ring;
at least one of $R_1$, $R_2$, $R_3$, $R_4$, $R_5$, $R_7$ and $R_8$ must be an amino group which on reacting with the cross-linking reagent gives rise to —NH—L or N=L group.

2. A method for preparing the reagents of claim 1, characterised by reacting together at least one compound chosen from each of the following classes:
(a) a protein;
(b) a dye chosen from those oxazines or thiazines which in the visible range have an absorption with $\lambda$ max between 550 and 800 nm, and which have at least one free $NH_2$, and a fluorescence with emission between 600 and 900 nm
(c) a cross-linking agent, generally in the form of bifunctional reagents of which the groups are able to react with the amino group of the dye.

3. A method for preparing reagents as claimed in claim 2, characterised in that the reaction between the three compounds can be carried out either starting from the substrates alone or in the presence of a medium compatible with the compounds.

4. A method for preparing reagents as claimed in claim 3, characterised in that the reaction is preferably carried out in the presence of water, or of aqueous solution of one or more salts, or of buffer mixture.

5. A method for preparing reagents as claimed in claim 3, characterised in that the reaction takes place at a pH which varies from 4.5 to 9.5.

6. A method for preparing reagents as claimed in claim 5, characterised in that the reaction temperature varies around ambient temperature.

7. A method for preparing reagents as claimed in claim 6, characterised in that the reaction temperature varies preferably between 4° C. and the protein denaturation temperature.

8. A method for preparing reagents as claimed in claim 7, characterised in that the reaction is carried out with a large excess of dye over the protein.

9. A method for preparing reagents as claimed in claim 8, characterised in that the reaction is varying from 4 to 50 times in terms of molar concentration.

10. A method for preparing reagents as claimed in claim 9, characterised in that the reaction is carried out with a large excess of the bifunctional agent over the total quantity of protein and dye taken together.

11. A method for preparing reagents as claimed in claim 1 wherein $R_3$ is an amino group.

* * * * *